US011103430B2

(12) United States Patent
Pan et al.

(10) Patent No.: US 11,103,430 B2
(45) Date of Patent: Aug. 31, 2021

(54) HIGH-PH ACTIVE COMPOSITIONS

(71) Applicant: Colgate-Palmolive Company, New York, NY (US)

(72) Inventors: Long Pan, Somerset, NJ (US); Scott Smart, Piscataway, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/760,307

(22) PCT Filed: Sep. 15, 2016

(86) PCT No.: PCT/US2016/051978
§ 371 (c)(1),
(2) Date: Mar. 15, 2018

(87) PCT Pub. No.: WO2017/048983
PCT Pub. Date: Mar. 23, 2017

(65) Prior Publication Data
US 2018/0263874 A1   Sep. 20, 2018

Related U.S. Application Data

(60) Provisional application No. 62/220,956, filed on Sep. 18, 2015.

(51) Int. Cl.
*A61Q 15/00* (2006.01)
*A61K 8/26* (2006.01)
*A61K 8/44* (2006.01)
*A61K 8/42* (2006.01)
*A61K 8/21* (2006.01)
*C02F 1/52* (2006.01)
*A61K 8/19* (2006.01)
*A61K 8/28* (2006.01)

(52) U.S. Cl.
CPC ............... *A61K 8/26* (2013.01); *A61K 8/19* (2013.01); *A61K 8/21* (2013.01); *A61K 8/28* (2013.01); *A61K 8/42* (2013.01); *A61K 8/44* (2013.01); *A61Q 15/00* (2013.01); *C02F 1/5245* (2013.01); *A61K 2800/58* (2013.01)

(58) Field of Classification Search
CPC ... A61K 8/26; A61K 8/44; A61K 8/42; A61K 2800/58; A61K 8/28; A61K 8/19; A61Q 15/00; C02F 1/5245
See application file for complete search history.

(56) References Cited

U.S. PATENT DOCUMENTS

| | | | | |
|---|---|---|---|---|
| 6,136,302 A * | 10/2000 | Juneja | ...................... | A61K 8/28 423/463 |
| 6,726,901 B2 * | 4/2004 | Yin | ...................... | A61Q 15/00 424/400 |
| 7,087,220 B2 | 8/2006 | Li | | |
| 7,105,691 B2 | 9/2006 | Holerca | | |
| 8,257,689 B2 | 9/2012 | Pan | | |
| 8,557,228 B2 | 10/2013 | Pan | | |
| 2005/0265939 A1 * | 12/2005 | Li | ...................... | A61K 8/28 424/65 |
| 2007/0003499 A1 | 1/2007 | Shen et al. | | |
| 2010/0202993 A1 | 6/2010 | Pan | | |
| 2011/0200545 A1 * | 8/2011 | Maniga | ...................... | C11D 7/265 424/65 |
| 2015/0132242 A1 * | 5/2015 | Yuan | ...................... | A61K 8/28 424/66 |

FOREIGN PATENT DOCUMENTS

| | | |
|---|---|---|
| CN | 1993097 | 7/2007 |
| CN | 101896156 | 11/2010 |
| CN | 103690384 | 4/2014 |
| CN | 103705390 | 4/2014 |
| RU | 2340596 | 12/2008 |
| RU | 2440092 | 1/2012 |
| RU | 2527693 | 9/2014 |
| WO | WO 2013158077 A1 * | 10/2013 |

OTHER PUBLICATIONS

Daniele Innocenzi, et al, Title: An open-label tolerability and efficacy study of an aluminum sesquichlorhydrate topical foam in axillary and palmar primary hyperhidrosis; Dermatologic therapy, vol. 21, Issues 1, Jul./Aug. 2008, p. S27-30, first published: Jul. 22, 2008. (Year: 2008).*
Unknown, title: Aluminium Zirconium Tetrachlorohydrex Gly Properties, World of Chemiccals, downloaded from https://www.worldofchemicals.com/chemicals/chemical-properties/aluminium-zirconium-tetrachlorohydrex-gly.html on Jul. 10, 2019 (Year: 2019).*
Aluminum Sesquichlorohydrate, product information, downloaded from http://www.newdruginfo.com/pharmacopeia/usp28/v28230/usp28nf23s0_m2285.htm on Apr. 28, 2020. (Year: 2020).*
International Search Report and Written Opinion of the International Searching Authority in International Application No. PCT/US2016/051978, dated Nov. 25, 2016.
Knunyants, ed., 1961, Brief Chemical Encyclopedia. vol. 1 "AE" /Ch.editor I.L. Knunyants.-M.:"Soviet Encyclopedia", 1262 p., p. 180.
Jakubke et al., 1985, "Amino acids Peptides Proteins," editorship of Yu.V. Mitina. -M.: "Mir", 82 S., S. 9-23.

* cited by examiner

*Primary Examiner* — Yanzhi Zhang

(57) ABSTRACT

The present invention provides active compositions that contain an aluminum system active, a buffer comprising urea or an amino acid in free or salt form; and a calcium ion source. The compositions are stable at high pH; i.e., at a pH above 4 or 5, reaching neutral or basic pH.

15 Claims, No Drawings

HIGH-PH ACTIVE COMPOSITIONS

BACKGROUND OF THE INVENTION

The pH of aluminum antiperspirant systems is said to be the primary factor in controlling many of the undesirable effects of antiperspirants, such as irritation, clothing damage, and historically, the high irritation caused by monomeric aluminum chloride (pH—2) prompted the development of partially hydrolyzed aluminum solutions (pH—2-5) as common antiperspirant actives. Increasing pH above this level results in the formation of aluminum hydroxides colloids, which create the plugs to stop sweat. As aluminum AP actives can only be delivered in their low pH form, formulation is often a problem, and high pH formulations with antiperspirant actives are not stable, and will quickly decompose the Al actives into $Al(OH)_3$ conglomerates. This problem is insurmountable with normal systems, as the fundamental understanding of the $Al(OH)_3$ plug mechanism is that changes in pH drive the transformation from partially hydrolyzed aluminum species to fully hydrolyzed aluminum hydroxide plugs, whether through basic proteins or higher pH solutions.

Antiperspirant salts, such as aluminum chlorohydrex (also called aluminum chlorohydrex polymeric salts and abbreviated here as "ACH") and aluminum zirconium glycine salts (abbreviated here as "ZAG", "ZAG complexes" or "AZG"), are known to contain a variety of polymeric and oligomeric species with molecular weights (MW) of 100-500,000. It has been clinically shown that, in general, the smaller the species, the higher the efficacy for reducing sweat.

In an attempt to increase the quality and quantity of smaller aluminum and/or zirconium species, a number of efforts have focused on: (1) how to select the components of ACH and ZAG that affect the performance of these materials as antiperspirants; and (2) how to manipulate these components to obtain and/or maintain the presence of smaller types of these components. These attempts have included the development of analytical techniques to identify the components. Size exclusion chromatography ("SEC") or gel permeation chromatography ("GPC") are methods frequently used for obtaining information on polymer distribution in antiperspirant salt solutions. With appropriate chromatographic columns, generally five distinctive groups of polymer species can be detected in commercial ACH and ZAG complexes appearing in a chromatogram as peaks 1, 2, 3, 4 and a peak known as "5,6". Peak 1 is the larger Zr species (greater than 60 Angstroms). Peaks 2 and 3 are larger aluminum species. Peak 4 is smaller aluminum species (aluminum oligomers, or small aluminum cluster) and has been correlated with enhanced efficacy for both Al and Al/Zr salts. Peak 5, 6 is the smallest aluminum species. Various analytical approaches for characterizing the peaks of ACH and various types of ZAG actives are found in "Antiperspirant Actives—Enhanced Efficacy Aluminum-Zirconium-Glycine (AZG) Salts" by Dr. Allan H. Rosenberg (Cosmetics and Toiletries Worldwide, Fondots, D. C. ed., Hartfordshire, UK: Aston Publishing Group, 1993, pages 252, 254-256).

Previously, the inventor has described an aluminum salts having SEC chromatogram exhibiting high SEC peak 4 intensity in WO2009/075678 and WO2009/076591. As a byproduct of making these compositions using an alkaline earth metal base, an alkaline earth metal salt is generated. When the salt is an alkaline earth metal halide, it is difficult to dry the material because the salt is hygroscopic. An improved process for preparing the salt was developed which is disclosed in WO/2013/158077, and which uses a basic organic buffer (arginine) to reduce the amount of alkaline earth metal base/salt (calcium hydroxide) in the reaction so that there is less alkaline earth metal chloride (calcium chloride) in the reaction product, thus affording easier drying of the aluminum salt. Significantly, the pH of the process is intentionally kept low, to prevent degradation of the aluminum chlorohydrate, which is known to occur at higher pH.

There is a need for means of obtaining aluminum antiperspirant actives outside of the known ranges of stability, and that overcome the undesirable effects of traditional low-pH antiperspirants, and that have enhanced flocculation properties when used in water purification processes.

BRIEF SUMMARY OF THE INVENTION

The present invention provides antiperspirant active compositions that are stable at high pH; i.e., at a pH of above 4 or above 5, for example from pH 4 or 5 to about pH 11 or 12. The actives contain an amino acid, preferably arginine, a calcium ion source, and an aluminum system such as an aluminum chlorohydrate (ACH, e.g., aluminum monochlorohydrate, aluminum sesquichlorohydrate, or aluminum dichlorohydrate) active, and/or aluminum zirconium glycine salts (abbreviated here as "ZAG", "ZAG complexes" or "AZG").

It has been surprisingly found that the inclusion of high concentrations of an amino acid, in free or salt form, e.g. a basic amino acid such as arginine, in a system including an aluminum active where calcium ions, e.g. as $Ca(OH)_2$ or $CaCl_2$, are also present, allows the composition to maintain stability at high pH; e.g. greater than about pH 4; or greater than about pH 5 or about 6; e.g., as high as 10 or 11. Compositions containing the actives of the invention are effective and afford benefits over the traditional acidic antiperspirant compositions, including avoiding the deleterious consequences of contact with acidic antiperspirant with clothes, and benefits in reduced skin irritation. In some embodiments, the aluminum chlorohydrate active is aluminum sesquichlorohydrate. In some such embodiments, the compositions include a metal salt stabilizer and contain primarily peaks 3 and 4 under SEC, and maintaining a small particle size distribution.

The compositions of the invention are stable at high pH, i.e., at or above pH 4, at or above pH 5, e.g., up to pH 11 or 12.

The present disclosure also provides for antiperspirants and oral care compositions, e.g., dentifrices and mouth rinses, comprising the actives of the invention. Such compositions are particularly useful for the prevention or treatment of dental hypersensitivity.

The present disclosure also provides methods for making the compositions of the invention.

DETAILED DESCRIPTION OF THE INVENTION

As used throughout, ranges are used as a shorthand for describing each and every value that is within the range. Any value within the range can be selected as the terminus of the range.

The present invention is directed to actives; e.g., antiperspirant and oral care actives, that are stable at high pH. In a first embodiment, the present disclosure provides an antiperspirant or oral care active 1.0 comprising:

I. an aluminum system active, comprising one or both of:
   an aluminum containing active comprising chloride ions, and having a metal (i.e., aluminum) to chloride ratio of from 0.3 to 3; and/or
   an aluminum active comprising or derived from aluminum zirconium glycine salts (abbreviated herein as "ZAG", "ZAG complexes" or "AZG");
II. a buffer comprising urea or an amino acid in free or salt form, e.g., a basic amino acid, e.g., arginine or lysine; and
III. a calcium ion source, e.g. $CaCl_2$ or $Ca(OH)_2$;
   wherein the composition has a pH of about 5 or greater; or about 6 or greater;
   and wherein the aluminum active is stable at the pH; for example:

1.1 active 1.0, wherein the aluminum active comprises chloride ions and has a metal to chloride ratio of 0.33;

1.2 active 1.0, wherein the aluminum active comprises chloride ions and has a metal to chloride ratio of 3, or of 0.42, or of 0.4, or of 0.3.

1.3 active 1.0, wherein the aluminum active comprises or is derived from aluminum chloride or aluminum chlorohydrate (e.g., aluminum mono chlorohydrate, aluminum sesquichlorohydrate, or aluminum dichlorohydrate);

1.4 active 1.0, wherein the active aluminum system comprises or is derived from aluminum chlorohydrate;

1.5 active 1.3, wherein the aluminum chlorohydrate active comprises or is derived from aluminum monochlorohydrate, aluminum dichlorohydrate, or aluminum sesquichlorohydrate;

1.6 active 1.4, wherein the aluminum active comprises or is derived from aluminum sesquichlorohydrate;

1.7 active 1.4, wherein the aluminum active is derived from $AlCl_3$, glycine, and $CaCO_3$ or $Ca(OH)_2$, where the final composition is about 3-4% Al, about 6-7% Ca, and about 8-9% Gly; e.g., about 3.75% Al, about 6.54% Ca, and about 8.80% Gly (referred to herein as EACH);

1.8 active 1.6 or 1.7, wherein the aluminum active comprises from about 12% to about 14% EACH; and from about 0.1% to about 50% arginine; or from about 0.1% to about 45% arginine; or about 10% to about 45% arginine; or about 20% to about 45% arginine; or about 30% to about 45% arginine; or about 35% to about 45% arginine; or about 40% to about 45% arginine;

1.9 active 1.8, wherein the aluminum active comprises from about 12% to about 14% EACH; and from about 35% to about 45% arginine;

1.10 any of actives 1.8-1.9, wherein the EACH has an aluminum to chloride molar ratio of about 0.3 to about 3, and exhibits a SEC chromatogram having a SEC Peak 4 to Peak 3 intensity ratio of at least 7 and a Peak 4 intensity greater than a Peak 5 intensity in aqueous solution, and optionally includes zirconium;

1.11 any of actives 1.0-1.6, wherein the aluminum active comprises an aluminum chloride compound having an aluminum to chloride molar ratio of 0.3:1 to 3:1 exhibiting a Size Exclusion Chromatography (SEC) chromatogram having a SEC Peak 4 to Peak 3 intensity ratio of at least 7 and a Peak 4 intensity greater than a Peak 5 intensity in aqueous solution.

1.12 any of actives active 1.0-1.11, further comprising zirconium in a molar ratio of aluminum to zirconium of about 5:1 to about 10:1;

1.13 any of actives 1.0-1.6, wherein the aluminum active comprises an aluminum salt and/or aluminum-zirconium salt, that exhibits, in aqueous solution, a SEC profile wherein the SEC Peak 4 to Peak 3 intensity ratio is at least 7.

1.14 active 1.13, wherein the percentage of SEC Peak 4 of a total area of Peaks 1, 2, 3, 4, 5, and 6 in the SEC chromatogram is: at least 50%; at least 60%; at least 70%; at least 80%; at least 90%; 95 to 100%; or 100%.

1.15 any of actives 1.0-1.3, wherein the aluminum active comprises aluminum chlorohydrate (ACH);

1.16 active 1.15, wherein the aluminum active is selected from the group consisting of aluminum monochlorohydrate, aluminum dichlorohydrate, aluminum sesquichlorohydrate, complexed or uncomplexed aluminum chlorohydrate, aluminum chlorohydrex polyethylene glycol, aluminum chlorohydrex propylene glycol, complexed or uncomplexed aluminum dichlorohydrate, aluminum dichlorohydrex polyethylene glycol, aluminum dichlorohydrex propylene glycol, complexed or uncomplexed aluminum sesquichlorohydrate, aluminum sesquichlorohydrex polyethylene glycol, aluminum sesquichlorohydrex propylene glycol, complexed or uncomplexed aluminum zirconium octachlorohydrate, aluminum zirconium octachlorohydrex glycine, aluminum zirconium pentachlorohydrate, aluminum zirconium pentachlorohydrex glycine, complexed or uncomplexed aluminum zirconium tetrachlorohydrate, aluminum zirconium tetrachlorohydrex glycine, complexed or uncomplexed aluminum zirconium trichlorohydrate, and aluminum zirconium trichlorohydrex glycine;

1.17 active 1.15 or 1.16, wherein the aluminum chlorohydrate active has a composition comprising 24-27% Al, 15-18% Cl, and wherein 45-50% of the composition is present as $Al_2O_3$;

1.18 active 1.17 wherein the aluminum chlorohydrate active has a composition comprising 25-26% Al, 16-17% Cl, and wherein 48-49% of the composition is present as $Al_2O_3$;

1.19 Active 1.15 or 1.16, wherein the aluminum chlorohydrate active has a composition comprising 6-8% Ca, 3-5% Al, 14-17% Cl, 13-17% Arginine, and 15-17% of an active ACH having 25-26% Al, 16-17% Cl, and wherein 48-49% of the composition is present as $Al_2O_3$;

1.20 Active 1.15 or 1.16, wherein the aluminum chlorohydrate active has a composition comprising 7-8% Ca, 3.5-4.5% Al, 15-16% Cl, 14-16% Arginine, and 15-16% of an active ACH having 25-26% Al, 16-17% Cl, and wherein 48-49% of the composition is present as $Al_2O_3$;

1.21 Active 1.15 or 1.16, wherein the aluminum chlorohydrate active has a composition comprising about 7.25% Ca, about 4% Al, about 15.5% Cl, about 15% Arginine, and about 15.9% of an active ACH having 25-26% Al, 16-17% Cl, and wherein 48-49% of the composition is present as $Al_2O_3$;

1.22 active 1.15 or 1.16, wherein the aluminum chlorohydrate active has a composition comprising 3-7% Ca, 35-45% arginine, 2-6% Al, and 9-30% of an ACH having 25-26% Al, 16-17% Cl, and wherein 48-49% of the composition is present as $Al_2O_3$;

1.23 active 1.16 wherein the aluminum chlorohydrate active has a composition comprising 4-5% Ca, 35-40% arginine, 2-3% Al, and 10-11% of an ACH having 25-26% Al, 16-17% Cl, and wherein 48-49% of the composition is present as $Al_2O_3$;

1.24 active 1.16 wherein the aluminum chlorohydrate active has a composition comprising about 4.5% Ca, about 38-39% arginine, 2-3% Al, and 10.0-10.5% of an ACH having 25-26% Al, 16-17% Cl, and wherein 48-49% of the composition is present as $Al_2O_3$;

1.25 active 1.16 wherein the aluminum chlorohydrate active has a composition comprising 5-6% Ca, 40-45% arginine, 2.5-3.5% Al, and 11.5-12.5% of an ACH having 25-26% Al, 16-17% Cl, and wherein 48-49% of the composition is present as $Al_2O_3$;

1.26 active 1.16 wherein the aluminum chlorohydrate active has a composition comprising about 5.3% Ca, about 42-43% arginine, about 3% Al, and about 11.8-12.0% of an ACH having 25-26% Al, 16-17% Cl, and wherein 48-49% of the composition is present as $Al_2O_3$;

1.27 any of actives 1.22-1.26 wherein the ACH comprises about 25.6% Al, about 16.7% Cl, and wherein about 48.3% of the composition is present as $Al_2O_3$;

1.28 any of actives 1.0-1.27 wherein the active is prepared by a method comprising the steps of:
preparing a solution comprising the aluminum active and the calcium ion source; and
adding the buffer to the solution to form a second solution;

1.29 active 1.28, wherein the buffer comprises or consists of arginine.

1.30 active 1.28 or 1.29, wherein the calcium ion source comprises $CaCl_2$;

1.31 active 1.28 or 1.29, wherein the calcium ion source comprises $Ca(OH)_2$;

1.32 any of actives 1.28-1.31, wherein the method further comprises the step of heating the second solution.

1.33 any of actives 1.28-1.32, wherein the method further comprises the step of adjusting the pH of the second solution to a pH of 5-12, for example a pH of 5-11, for example a pH of 5-10, 6-10, or about 6, about 7, about 8, about 9, about 10, or about 11;

1.34 any of actives 1.0-1.2 or 1.28-1.31, wherein the aluminum active comprises or consists of aluminum chloride.

1.35 any of actives 1.0-1.34, wherein the aluminum active is present in an amount of from about 5% to about 20%; or from about 7% to about 15%; or from about 7% to about 12%; of the composition by weight.

1.35 any of the foregoing actives 1.0-1.29 or 1.34, wherein the calcium ion source comprises $CaCl_2$, $Ca(OH)_2$, or $CaCO_3$;

1.36 any of the foregoing actives 1.0-1.35, wherein the buffer is or comprises one or more amino acids in free or salt form;

1.37 active 1.36, wherein the amino acids are selected from alpha amino acids and their salt forms.

1.38 active 1.36, wherein the amino acids are selected from alpha amino acids, and their salt forms;

1.39 active 1.36, wherein the amino acids are selected from basic amino acids, neutral amino acids, and their salt forms;

1.40 active 1.36, wherein the amino acids are selected from arginine, lysine, glycine and their salt forms;

1.41 active 1.36, wherein the buffer comprises arginine, lysine or their salt forms;

1.42 active 1.36, wherein the buffer comprises arginine and/or a salt form thereof;

1.43 any of the foregoing actives 1.0-1.35, wherein the aluminum active comprises an aluminum zirconium glycine salt;

1.44 any of the foregoing actives 1.0-1.35, wherein the aluminum active comprises zirconium in a molar ratio of aluminum to zirconium of about 5:1 to about 10:1;

1.45 any of actives 1.0-1.14, wherein the aluminum active comprises aluminum sesquichlorohydrate, and is prepared according to a method comprising:
i) heating an aqueous solution of an aluminum chloride compound having an aluminum to chloride molar ratio of 0.3:1 to 3:1 to a temperature of at least 50° C. for a period of time of at least 1 hour;
ii) providing an aqueous solution containing a source of an alkaline earth metal to obtain a pH adjusted aluminum salt solution having a pH of 2 to 5; and
wherein at least one basic organic buffer is included with at least one of I) the aqueous solution of the aluminum and chloride containing salt, and II) the aqueous solution containing the alkaline earth metal, wherein the pH adjusted aluminum salt solution has an aluminum salt with an OH:Al molar ratio of 2:1 to 2.6:1, wherein a basic organic buffer to alkaline earth metal ion molar ratio is 0.22:1 to 18:1;
wherein the method optionally further comprises adding an aqueous solution containing a zirconium compound to the pH adjusted aluminum salt solution to thereby obtain an aluminum-zirconium salt solution having a molar ratio of aluminum to zirconium of 2:1 to 10:1, for example wherein the zirconium compound is $ZrOCl_2$.

1.46 active 1.45, wherein the molar ratio of basic organic buffer to alkaline earth metal ion is 0.3:1 to 18:1, for example 0.4:1 to 18:1, 0.5:1 to 18:1, 1:1 to 18:1, 1.5:1 to 18:1, 1.9:1 to 18:1, 2:1 to 18:1, 1:1 to 3:1, 1.5:1 to 3:1, 1.5:1 to 2.5:1, 1.5:1 to 2:1, 1.9:1 to 3:1, 1.9:1 to 2.5:1, or 1.9:1 to 2:1;

1.47 active 1.45 or 1.46, wherein the basic organic buffer is selected from the group consisting of arginine, lysine, histidine, cysteine, tyrosine, a salt form of any of the foregoing, and urea; for example wherein the basic organic buffer is arginine or a salt form thereof;

1.48 any of actives 1.45-1.47, wherein the alkaline earth metal is selected from the group consisting of calcium, strontium, and barium; for example wherein the alkaline earth metal is calcium;

1.49 any of active 1.45-1.48, wherein the aluminum chloride compound is chosen from aluminum trichloride, aluminum chlorohydrate, and aluminum dichlorohydrate; for example wherein the aluminum chloride compound is aluminum trichloride;

1.50 any of actives 1.45-1.49, prepared by a method comprising the steps of: a) combining $AlCl_3 \cdot 6H_2O$ and glycine in a solvent, which is preferably water, to form a solution thereof; b) adding calcium hydroxide or calcium carbonate, preferably calcium hydroxide to form a second solution; and c) adding arginine to the second solution;

1.51 any of actives 1.0-1.50, comprising from about 0.8 to about 1.2 M $Al^{+3}$ ions, for example from about 0.9 to about 1.1 M $Al^{+3}$ ions, for example about 1 M $Al^{+3}$ ions; from about 1 to about 1.4 M $Ca^{+2}$ ions, for example from about 1.1 to about 1.3 M $Ca^{+2}$ ions, for example about 1.2 M $Ca^{+2}$ ions; from about 1 to about 1.4 M glycine, for example from about 1.1 to about 1.3 M glycine, for example about 1.2 M glycine; and from about 0.05% to about 50% arginine, w/w;

1.52 any of actives 1.28-1.33 or 1.45-1.50, wherein the method further comprises the step of adjusting the pH to a value of 5, or greater than 5, in aqueous solution; for example a pH of from about 5 to about 11; or from about 5 to about 9; or from about 7 to about 10; from about 7 to about 9; or from about 7 to about 8 in aqueous solution.

1.53 any of actives 1.0-1.42 having a pH of 5, or greater than 5, in aqueous solution; for example a pH of from about 5 to about 9; from about 6 to about 10; or from about 7 to about 10; from about 7 to about 9; or from about 7 to about 8 in aqueous solution.

1.54 any of actives 1.0-1.53 wherein the ratio of the wt % of the amino acid to the wt % of the aluminum containing active is from 8:1 or lower, for example from 1:2 to 2:1; or from 3:1 to 5:1.

The present disclosure also provides an antiperspirant 1.0, comprising any of actives 1.0-1.54; for example:

1.1 antiperspirant 1.0, wherein the active comprises: from about 2% to about 8% w/w of $Al^{+3}$ ions, for example from about 2.5% to about 5.5% $Al^{+3}$ ions, for example about 3% $Al^{+3}$ ions; from about 3% to about 9% w/w $Ca^{+2}$ ions, for example from about 4% to about 7% $Ca^{+2}$ ions, for example about 4.5% to about 5.5% $Ca^{+2}$ ions for example, about 5.25% $Ca^{+2}$ ions; from about 9% to about 25% ACH, for example from about 10% to about 12.5% ACH, for example from about 11.5% to about 12.4% ACH, for example about 11.9% ACH; and from about 25% to about 60% arginine, w/w, for example about 30% to about 50% arginine; for example about 35% to about 45% arginine, for example from about 40% to about 45% arginine; for example about 43% arginine;

The present disclosure also provides an oral care composition 1.0, comprising an active according to any one of actives 1.0-1.54. The invention further includes a method of treating or preventing tooth sensitivity (Method 2.0) comprising contacting a tooth of a patient in need thereof with an oral care active according to any of actives 1.0-1.54, or a composition comprising any of the aforementioned actives.

The present disclosure also provides a method (Method 3.0) for the preparation of an antiperspirant or oral care aluminum containing active having a pH of about 5 or greater, or about 6 or greater; wherein the aluminum active is stable at the pH; comprising the steps of:
 preparing a solution comprising an aluminum active and a calcium ion source; and
  adding a buffer to the solution to form a second solution; wherein:
  the aluminum active either (i) comprises chloride ions, and has a metal to chloride ratio of from 0.3 to 3; and/or
   (ii) comprises or is derived from aluminum zirconium glycine salts; and
  the buffer comprises urea or an amino acid in free or salt form; for example:
  3.1 Method 3.0, wherein the buffer comprises arginine or a salt form thereof;
  3.2 Method 3.0 or 3.1, wherein the calcium ion source comprises $CaCl_2$;
  3.3 Method 3.0 or 3.1, wherein the calcium ion source comprises $Ca(OH)_2$;
  3.4 any Method 3.0-3.3, wherein the method further comprises the step of heating the second solution;
  3.5 any Method 3.0-3.4, further comprising the step of adjusting the pH of the second solution to a pH of 5-12, for example a pH of 5-11, for example a pH of 5-10, 5-9, 6-10, or about 6, about 7, about 8, about 9, about 10, or about 11;
  3.6 any Method 3.0-3.5, wherein the aluminum active comprises or consists of aluminum chloride;
  3.7 any Method 3.0-3.5, wherein the aluminum active comprises or consists of aluminum chlorohydrate;
  3.8 any Method 3.0-3.5, wherein the aluminum active comprises aluminum sesquichlorohydrate;
  3.9 Method 3.8, wherein the aluminum sesquichlorohydrate, prepared according to a method comprising:
   i) heating an aqueous solution of an aluminum chloride compound having an aluminum to chloride molar ratio of 0.3:1 to 3:1 to a temperature of at least 50° C. to reflux temperature for a period of time of at least 1 hour;
   ii) providing an aqueous solution containing a source of an alkaline earth metal to obtain a pH adjusted aluminum salt solution having a pH of 2 to 5; and wherein at least one basic organic buffer is included with at least one of I) the aqueous solution of the aluminum and chloride containing salt, and II) the aqueous solution containing the alkaline earth metal, wherein the pH adjusted aluminum salt solution has an aluminum salt with an OH:Al molar ratio of 2:1 to 2.6:1, wherein a basic organic buffer to alkaline earth metal ion molar ratio is 0.22:1 to 18:1;

wherein the method optionally further comprises adding an aqueous solution containing a zirconium compound to the pH adjusted aluminum salt solution to thereby obtain an aluminum-zirconium salt solution having a molar ratio of aluminum to zirconium of 2:1 to 10:1, for example wherein the zirconium compound is $ZrOCl_2$.

The present disclosure also provides a method of preventing or controlling perspiration (Method 4.0) comprising contacting the skin of a person with an antiperspirant composition 1.0, or an antiperspirant active according to any of actives 1.0-1.54.

The present disclosure also provides a method of treating polluted water comprising contacting the water with an active according to any of actives 1.0-1.54.

The present invention provides for aluminum antiperspirant active compositions stable at high pH. As used herein, high pH means a pH of 5 or above, for example pH 5, 6, 7, 8, 9, 10 or 11.

It has been discovered in accordance with the present invention that the inclusion of high concentrations of an amino acid, in free or salt form, e.g. a basic amino acid such as arginine, or urea, in a system including an aluminum active where calcium ions, e.g. as $Ca(OH)_2$ or $CaCl_2$, are also present, allows the composition to maintain stability at high pH; e.g. greater than about pH 4; or greater than about pH 5 or about 6; e.g., as high as 10 or 11.

Actives:

The invention is amenable to a wide variety of aluminum-containing actives, including virtually all known antiperspirant aluminum-containing actives. Thus, in one embodiment, the invention provides a high-pH antiperspirant or oral care active comprising an aluminum-containing active, such as are employed in currently marketed antiperspirant compositions, for example and not limitation the aluminum chlorohydrate salts approved for use as antiperspirants in the United States are listed in 21 CFR 350.10, and a buffer comprising urea or an amino acid in free or salt form, e.g., a basic amino acid, e.g., arginine or lysine; and a calcium ion source, e.g. $CaCl_2$ or $Ca(OH)_2$; wherein the composition has a pH of about 5 or greater; or about 6 or greater; and wherein the aluminum active is stable at the pH.

The aluminum-containing active can be any of a wide variety of aluminum-containing antiperspirant actives. Non-limiting examples include aluminum-containing actives that contain chloride ions, and a metal (i.e., aluminum) to chloride ratio of from 0.3 to 3. Exemplary actives include actives based on aluminum chloride and/or aluminum chlorohydrate (ACH), as well as other aluminum-containing actives such as ZAG.

Aluminum chlorohydrate is an aluminum salt formed from aluminum or aluminum hydroxide, hydrochloric acid, and water, and optionally also including zirconium and/or complexing agents such as amino acids or polyols. Such salts are used in deodorants and antiperspirants, and as coagulants or flocculants in water purification processes. In aqueous solution, these salts form complex substructures, e.g., $Al_{13}$ units with a Keggin ion structure, which in turn form larger polymeric species with molecular weights (MW) of over 1000 Daltons. The precise ratios of elements in these salts and the precise three dimensional structures formed can be controlled by method of manufacture. Typically, aluminum chlorohydrate salts may have the general formula $Al_nCl_{(3n-m)}(OH)_m$, e.g., $Al_n(OH)_m(Cl)_n$, where m+n=6; e.g., $Al_2Cl(OH)_5$ or $Al_4Cl_2(OH)_{10}$. See Fitzgerald and Rosenberg, "Chemistry of Aluminum Chlorohydrate and Activated Aluminum Chlorohydrates", Chapter 4, "Antiperspirants and Deodorants" by Karl Lader, Cosmetics Science and technology Series, V.20, $2^{nd}$. Rev., Marcel Dekker, 1999, pages 83-135, incorporated herein in its entirety for all purposes. These salts may additionally be in complex with zirconium and/or an amino acid, ammonium acid, or a polyol, e.g., Al/Zr tetrachlorohydrex-Gly ($[Al_4Cl_2(OH)_{10}.ZrOCl_2] NH_2CH_2COOH$). Aluminum chlorohydrate salts approved for use as antiperspirants in the United States are listed in 21 CFR 350.10, each of which is amendable to use in the present invention.

Size exclusion chromatography ("SEC") or gel permeation chromatography ("GPC") provides information on polymer distribution of aluminum chlorohydrate in aqueous solutions. For antiperspirant salts generally, including aluminum chlorohydrate, aluminum/zirconium chlorohydrate, and complexes thereof, distinctive peaks have been identified, corresponding to different size populations of the polymer complexes in solution, appearing in a chromatogram as peaks 1, 2, 3, 4 and a peak known as "5,6". Peak 1 is the larger Zr species (greater than 60 Angstroms), and is not present in salts without zirconium. Peaks 2 and 3 are larger aluminum species. Peak 4 is a smaller aluminum species (aluminum oligomers, or small aluminum cluster) and has been correlated with enhanced efficacy for both Al and Al/Zr salts. Peak 5, 6 is the smallest aluminum species.

Aluminum chlorohydrate salts used in commercial antiperspirant formulations are typically activated or enhanced to contain large amounts of Peak 4 species. Commonly, such salts further comprise zirconium and glycine, and are sometimes referred to as zirconium-aluminum chlorohydrex glycine ("ZAG" or "AZG").

The levels of molecular species in compositions of the invention can be ascertained SEC tracing. The SEC technique is explained fully in PCT/US2012/033926 and U.S. 2015/0132242 each of which is incorporated by reference herein in its entirety for all purposes.

Aluminum chlorohydrate salts are known to be stable only at relatively low pH values, e.g., pH values less than 5, and loser to pH 4 or less. At higher pH values, the ACH begins to break down. All known aluminum based antiperspirant actives obey the relation wherein an increase in pH, which is proportional to the increase in concentration of base (i.e., increase in [OH$^-$]), produces a proportional increase in the ratio of [OH] to [Al], ("the hydrolysis ratio"), which results in the formation of $Al(OH)_3$, which forms aggregates. Thus, when such aluminum based antiperspirant actives, having low pH (e.g., 2-4) are on the skin, the higher pH of skin (approx. pH 5.5) causes the actives to interact with proteins and other salts in the skin to form precipitate in the form of $Al(OH)_3$ through a series of hydrolysis reactions. $Al(OH)_3$ forms as large aggregates which are effective as plugs, are unreactive, and which are removed by sweating.

The compositions of the present disclosure surprisingly do not obey this relationship. Rather, for the present composition, it is believed that the increase in pH and [OH$^-$] does not result in a proportional increase in the hydrolysis ratio [OH]/[Al]. While not wishing to be bound by a particular theory, it is believed that the amino acid, e.g. the basic amino acid, e.g. arginine, in conjunction with the alkaline earth metal shields the actives from being hydrolyzed, and makes them stable for traditional use at different pH values. It is believed that complexation of the basic amino acid, e.g. arginine, with the aluminum salt cationic clusters and the alkaline earth metals stabilizes them against decomposition and/or hydrolysis that would otherwise occur at high pH. Improper preparation of the material can result in the typical hydrolysis occurring. Thus, the present actives can be prepared and employed, and remain stable, at pH ranges where the traditional aluminum actives are unstable, such as, for example at the pH of human skin. The compositions of this invention may therefore be used to formulate antiperspirants having improved stability and efficacy at high pH.

Buffers:

The buffers of the present compositions can include urea, or an amino acid in free or salt form. As use herein, the term "amino acid" is intended to mean a compound both amino (i.e., -NH$_2$) and acid (i.e., -C(=O)OH) functionality. In some embodiments, the amino acids can be alpha, beta, gamma or delta amino acids, and their salt forms, and also include any D, L and/or racemic forms, where the amino acid is capable of stereoisomerism. Alpha amino acids are known as compounds that have an amino moiety and a carboxyl moiety attached to the same (alpha) carbon atom.

In some embodiments, the buffer comprises one or more alpha amino acids, for example one or more of the twenty amino acids that are known in proteins. These include the aliphatic amino acids alanine, glycine, isoleucine, leucine, valine and proline; the aromatic amino acids phenylalanine, tryptophan and tyrosine; the acidic amino acids aspartic acid and glutamic acid; the basic amino acids arginine, histidine and lysine; the hydroxic amino acids serine and threonine; the sulfur-containing amino acids cysteine and methionine; and the amidic amino acids asparagine and glutamine. In some embodiments, the buffer comprises one or more of the basic amino acids; for example arginine or lysine; for example arginine, or their salt forms. As used herein, the salt forms of the amino acids include all salts of the amino acids, for example and not limitation Group I and Group II metal salts of acid functionalities of the amino acids, for example and not limitation calcium, magnesium, sodium, potassium, and chloride salts.

Calcium Ion Source

The actives of the present invention also include a calcium ion source, which can be any of a wide variety of calcium containing compounds. Nonlimiting examples of calcium ion sources include calcium chloride ($CaCl_2$), calcium carbonate (limestone, $CaCO_3$) or calcium hydroxide ($Ca(OH)_2$).

The antiperspirants of the present disclosure include solids such as sticks and creams (creams sometimes being included in the term "soft solid"), gels, liquids (such as are suitable for roll-on products), and aerosols. The forms of these products may be suspensions or emulsions. These antiperspirant actives can be used as the antiperspirant active in any antiperspirant composition.

Examples of Suitable Formulations

Sticks

Stick products may be made with conventional gelling agents such as stearyl alcohol and dibenzylidene sorbitol. A sample formulation is as follows:

40-55% cyclomethicone;
20-30% stearyl alcohol;
7-15% talc;
15-22%; antiperspirant active of the invention in particle form; and
1-3% fragrance.

Roll Ons

Roll Ons having a sample formulation:
45-65% cyclomethicone;
0.1-10% cyclomethicone/dimethicone copolyol
10-25% antiperspirant active of the invention in solution form (25-45% actives on an anhydrous basis in water); and
5-33% water and minors (color, fragrance, etc.).

Soft Solids

Soft solids may be made with formulations described in U.S. Pat. No. 6,682,749. A sample formulation is as follows:
40-70% elastomer in cyclomethicone;
5-15% polyethylene (for example, as beads);
10-20% C12-15 alkylbenzoate;
0.1-25% antiperspirant active of the invention in powder form;
1-15% dimethicone; and
1-3% minors (e.g., fragrance).

Gels

Gels may be made with a variety of formulations such as:
5-50% cyclomethicone;
0.1-10% cyclomethicone/dimethicone copolyol;
0-10% hydrogenated polyisobutene 250;
0-10% C12-15 alkylbenzoate;
0-10% dimethicone;
0.1-25% antiperspirant active of the invention in powder form or 10-25% of active in solution; and
6-53% water and minors (e.g., fragrance).

Note that in the explanation of the invention, where water is listed it is intended to count the contribution of the water present in the antiperspirant solution as part of the overall water content. Thus, water is sometimes listed as part of the actives solution or sometimes listed separately.

In one embodiment the refractive indices of the external and internal phases are matched within 0.005 to obtain a clear product.

Other Formulations of Interest

Formulation A
0.5-2.5% dimethicone copolyol;
55-65% elastomer in cyclomethicone;
1-10% PPG-3 myristyl ether;
10-25% antiperspirant active of the invention;
10-27% water and minors (e.g., fragrance).

Formulation B
1.0-3.0% dimethicone copolyol;
40-60% elastomer in cyclomethicone;
1-5% cyclomethicone (in addition to that found in the elastomer);
4-12% PPG-3 myristyl ether;
15-30% antiperspirant active of the invention;
15-37% water and minors (e.g., fragrance).

Formulation C
1.0-3.0% dimethicone copolyol;
1-10% hydrogenated polyisobutene;
40-55% elastomer in cyclomethicone;
3-8% PPG-3 myristyl ether;
15-20% antiperspirant active of the invention;
20-33% water and minors (e.g., fragrance).

Formulation D
1.0-3.0% dimethicone copolyol;
40-60% elastomer in cyclomethicone;
3-8% PPG-3 myristyl ether;
15-30% antiperspirant active of the invention;
15-32% water and minors (e.g., fragrance); and
1-10% diethylhexyl naphthalate.

Formulation E
0.5-2.5% dimethicone copolyol;
60-70% elastomer in cyclomethicone;
7-10% antiperspirant active of the invention;
25-37% water and minors (e.g., fragrance); and
1-10% methylpropylene diol (MPDiol).

Formulation F
1.0-3.0% dimethicone copolyol;
6-10% hydrogenated polyisobutene;
35-45% elastomer in cyclomethicone;
6-10% PPG-3 myristyl ether;
40-50% antiperspirant active of the invention as 43% active in water, with no additional water; and
0.5-1.0% minors (e.g., fragrance).

Formulation G
0.1-0.6% dimethicone copolyol;
4-7% hydrogenated polyisobutene;
40-50% elastomer in cyclomethicone;
4-7% PPG-3 myristyl ether;
40-50% antiperspirant active of the invention as 43% active in water with no additional water; and
0.5-1.0% minors (e.g., fragrance).

Formulation H
0.5-2.0% dimethicone copolyol;
1-7% hydrogenated polyisobutene;
40-50% elastomer in cyclomethicone;
45-55% antiperspirant active as 43% active of the invention in water with no additional water; and
0.5-1.5% minors (e.g., fragrance).

Formulation I
2-7% dimethicone copolyol;
0.1-1% Oleath-20;
1-5% C12-15 alkyl benzoate;
15-25% elastomer in cyclomethicone;
15-25% antiperspirant active of the present invention;
15-32% water and minors (e.g., fragrance).

The cosmetic composition according to the present invention can be packaged in conventional containers, using conventional techniques. Where a gel, cream or soft-solid cosmetic composition is produced, the composition can be introduced into a dispensing package (for example, conventional packages for gels with glide on applicators, jars where the gel or cream is applied by hand, and newer style packages having a top surface with pores) as conventionally done in the art. Thereafter, the product can be dispensed from the dispensing package as conventionally done in the art, to deposit the active material, for example, on the skin. For sticks, sprays, aerosols and roll-ons the compositions can be placed in a conventional types of container (with the inclusion of propellants in aerosols). This provides good deposition of the active material on the skin.

Compositions of the present invention can be formulated as clear, translucent or opaque products. A desired feature of the present invention is that a clear, or transparent, cosmetic composition, (for example, a clear or transparent deodorant or antiperspirant composition) can be provided. The term clear or transparent according to the present invention is intended to connote its usual dictionary definition; thus, a clear liquid or gel antiperspirant composition of the present invention allows ready viewing of objects behind it. By contrast, a translucent composition, although allowing light to pass through, causes the light to be scattered so that it will be impossible to see clearly objects behind the translucent composition. An opaque composition does not allow light to pass there through. Within the context of the present invention, a gel or stick is deemed to be transparent or clear if the maximum transmittance of light of any wavelength in the range 400-800 nm through a sample 1 cm thick is at least 35%, or at least 50%. The gel or liquid is deemed translucent if the maximum transmittance of such light through the sample is between 2% and less than about 35%. A gel or liquid is deemed opaque if the maximum transmittance of light is less than about 2%. The transmittance can be measured by placing a sample of the aforementioned thickness into a light beam of a spectrophotometer whose working range includes the visible spectrum, such as a Bausch & Lomb Spectronic 88 Spectrophotometer. As to this definition of clear, see European Patent Application Publication No. 291,334 A2. Thus, according to the present invention, there are differences between transparent (clear), translucent and opaque compositions.

Oral Care:

The actives of the invention can be incorporated into oral care compositions, for example in compositions for alleviating dental hypersensitivity. Exemplary methods and formulations can be found in, for example PCT/US2013/032391 (U.S. Ser. No. 14/770,142, filed Aug. 25, 2015), which are incorporated herein by reference for all purposes.

In general, in addition to the actives of the invention, the present oral care compositions (e.g., dentifrices and mouth rinses) can contain one or more of the following components:

Fluoride Ion Source:

In some embodiments, the compositions may further include one or more fluoride ion sources, e.g., soluble fluoride salts. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as combinations thereof.

In certain embodiments, the oral care composition of the invention may contain a source of fluoride ions or fluorine-providing ingredient in amounts sufficient to supply 25 ppm to 25,000 ppm of fluoride ions, generally at least 500 ppm, e.g., 500 to 2000 ppm, e.g., 1000 to 1600 ppm, e.g., 450 ppm. The appropriate level of fluoride will depend on the particular application. A mouthrinse or mouthwash, for example, would typically have 100 to 250 ppm fluoride. A toothpaste for general consumer use would typically have 1000 to 1500 ppm, with pediatric toothpaste having somewhat less. A dentifrice or coating for professional application could have as much as about 5,000 or even about 25,000 ppm fluoride.

Fluoride ion sources may be added to the compositions of the invention at a level of 0.01 wt % to 10 wt % in one embodiment or 0.03 wt % to 5 wt %, and in another embodiment 0.1 wt % to 1 wt % by weight of the composition in another embodiment. Weights of fluoride salts to provide the appropriate level of fluoride ion will obviously vary based on the weight of the counter ion in the salt.

Abrasives:

In some embodiments, the oral care composition further comprises an abrasive. In some embodiments, the abrasive is selected from sodium bicarbonate, calcium phosphate (e.g., dicalcium phosphate dihydrate), calcium sulfate, precipitated calcium carbonate, silica (e.g., hydrated silica), iron oxide, alumina (e.g., coated alumina), perlite, zirconium silicate, a plastic particle, e.g., polyethylene, and a combination of two or more thereof. In some embodiments, the abrasive is present in the amount of 15 wt % to 70 wt % of the total composition weight.

In some embodiments, the compositions of the present invention may comprise a calcium phosphate abrasive, e.g., tricalcium phosphate ($Ca_3(PO4)2$), hydroxyapatite ($Ca_{10}(PO4)6(OH)_2$), or dicalcium phosphate dihydrate ($CaHPO_4.2H_2O$, also sometimes referred to herein as DiCal) or calcium pyrophosphate. Some embodiments may include one or more additional abrasives, for example silica abrasives such as precipitated silicas having a mean particle size of up to about 20 microns, such as Zeodent 115®, marketed by J. M. Huber. Other useful abrasives also include sodium metaphosphate, potassium metaphosphate, aluminum silicate, calcined alumina, bentonite or other siliceous materials, or combinations thereof.

The silica abrasive polishing materials useful herein, as well as the other abrasives, generally have an average particle size ranging between about 0.1 and about 30 microns, about between 5 and about 15 microns. The silica abrasives can be from precipitated silica or silica gels, such as the silica xerogels described in U.S. Pat. No. 3,538,230, to Pader et al. and U.S. Pat. No. 3,862,307, to Digiulio, both incorporated herein by reference. Particular silica xerogels are marketed under the trade name Syloid® by the W. R. Grace & Co., Davison Chemical Division. The precipitated silica materials include those marketed by the J. M. Huber Corp. under the trade name Zeodent®, including the silica carrying the designation Zeodent 115 and 119. These silica abrasives are described in U.S. Pat. No. 4,340,583, to Wason, incorporated herein by reference.

In certain embodiments, the silicas are colloidal particles having an average particle size of about 3 microns to about 12 microns, and about 5 to about 10 microns.

In particular embodiments, the abrasive materials comprise a large fraction of very small particles, e.g., having a d50<5 microns, for example, small particle silica (SPS) having a d50 of about 3 to about 4 microns, for example Sorbosil AC43® (Ineos). Such small particles are particularly useful in formulations targeted at reducing hypersensitivity. The small particle component may be present in combination with a second larger particle abrasive. In certain embodiments, for example, the formulation comprises about 3 to about 8% SPS and about 25 to about 45% of a conventional abrasive.

Low oil absorption silica abrasives particularly useful in the practice of the invention are marketed under the trade designation Sylodent XWA® by Davison Chemical Division of W.R. Grace & Co., Baltimore, Md. 21203. Sylodent 650 XWA®, a silica hydrogel composed of particles of colloidal silica having a water content of 29% by weight averaging about 7 to about 10 microns in diameter, and an oil absorption of less than about 70 cc/100 g of silica is an example of a low oil absorption silica abrasive useful in the practice of the present invention. The abrasive is present in the oral care composition of the present invention at a concentration of 10 to 60 wt %, in other embodiment 20 to 45 wt %, and in another embodiment 30 to 50 wt %.

Surfactants:

The compositions useful in the invention may contain anionic surfactants. The anionic surfactant may be present in an amount which is effective, e.g., >0.01 wt % of the composition, but not at a concentration which would be irritating to the oral tissue, e.g., <10 wt %, and optimal concentrations depend on the particular formulation and the particular surfactant. For example, concentrations used or a mouthwash are typically on the order of one tenth that used for a toothpaste. In one embodiment, the anionic surfactant is present in a toothpaste at from 0.3 to 4.5 wt %, e.g., about 1.5 wt %.

The compositions of the invention may optionally contain mixtures of surfactants, comprising anionic surfactants and other surfactants which may be anionic, cationic, zwitterionic or nonionic. Generally, surfactants are those which are reasonably stable throughout a wide pH range.

One nonlimiting example of suitable surfactant is sodium lauryl sulfate.

The surfactant or mixtures of compatible surfactants can be present in the compositions of the present invention in 0.1 to 5.0 wt %, in another embodiment 0.3% to 3.0 wt % and in another embodiment 0.5% to 2.0 wt % based on the total composition.

Some embodiments of the oral care composition of the invention comprise an anionic surfactant selected from:
 a. water-soluble salts of higher fatty acid monoglyceride monosulfates (e.g., the sodium salt of the monosulfated monoglyceride of hydrogenated coconut oil fatty acids such as sodium N-methyl N-cocoyl taurate, sodium cocomonoglyceride sulfate),
 b. higher alkyl sulfates, e.g., sodium lauryl sulfate,
 c. higher alkyl-ether sulfates, e.g., of formula $CH_3(CH_2)_m CH_2(OCH_2CH_2)_n OSO_3X$, wherein m is 6-16, e.g., 10, n is 1-6, e.g., 2, 3 or 4, and X is Na or K (for example sodium laureth-2 sulfate ($CH_3(CH_2)_{io}CH_2(OCH_2CH_2)_2OSO_3Na$)),
 d. higher alkyl aryl sulfonates (such as sodium dodecyl benzene sulfonate (sodium lauryl benzene sulfonate)),
 e. higher alkyl sulfoacetates (such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate),
 f. and mixtures thereof.

By "higher alkyl" is meant, e.g., $C_{6-30}$ alkyl. In particular embodiments, the anionic surfactant is selected from sodium lauryl sulfate and sodium ether lauryl sulfate. In some embodiments, the anionic surfactant is present in an amount of from 0.3 wt % to 4.5 wt % based on the total weight of the composition.

Humectants:

Some embodiments of the oral care composition of the invention may further comprise at least one humectant. Optionally, the humectant may be selected from glycerin, sorbitol, xylitol and combinations thereof.

Within certain embodiments of the oral compositions, it is also desirable to incorporate a humectant to prevent the composition from hardening upon exposure to air. Certain humectants can also impart desirable sweetness or flavor to dentifrice compositions. The humectant, on a pure humectant basis, generally includes from 15 to 70 wt % in one embodiment or from 30 to 65 wt % in another embodiment by weight of the oral care composition.

Suitable humectants include edible polyhydric alcohols such as glycerine, sorbitol, xylitol, propylene glycol as well as other polyols and mixtures of these humectants. Mixtures of glycerine and sorbitol may be used in certain embodiments as the humectant component of the toothpaste compositions herein.

Polymers/Gums:

Some embodiments of the oral care compositions of the invention may further comprise at least one polymer. Optionally, the at least one polymer may be selected from a polyethylene glycol, a polyvinylmethyl ether maleic acid copolymer, a polysaccharide (e.g., a cellulose derivative, for example carboxymethyl cellulose, or a polysaccharide gum, for example xanthan gum or carrageenan gum), and a combination of two or more thereof.

Some embodiments of the oral care composition of the invention may further comprise gum strips or fragments. Some embodiments of the oral care composition of the invention may further comprise flavoring, fragrance and/or coloring.

Antibacterial Agents:

Some embodiments of the oral care composition of the invention may further comprise comprising an antibacterial agent selected from a halogenated diphenyl ether (e.g. triclosan), a herbal extract and an essential oil (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), a bisguanide antiseptics (e.g., chlorhexidine, alexidine or octenidine), a quaternary ammonium compound (e.g., cetylpyridinium chloride (CPC), benzalkonium chloride, tetradecylpyridinium chloride (TPC), N-tetradecyl-4-ethylpyridinium chloride (TDEPC)), a phenolic antiseptic, hexetidine, octenidine, sanguinarine, povidone iodine, delmopinol, salifluor, a metal ion (e.g., zinc salts, for example, zinc citrate, stannous salts, copper salts, iron salts), sanguinarine, propolis and an oxygenating agent (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, a nicin preparation, a chlorite salt; and a combination of two or more thereof.

Some embodiments of the oral care composition of the invention further comprise an antibacterial agent in an amount of 0.01 to 5 wt % of the total composition weight. Some embodiments further comprise triclosan in an amount of 0.01 to 1 wt % of the total composition.

Calcium/Phosphate Sources

Some embodiments of the oral care composition of the invention can further comprise a source of calcium and phosphate (in addition to the calcium of the active) selected from (i) calcium-glass complexes, e.g., calcium sodium phosphosilicates, and (ii) calcium-protein complexes, e.g., casein phosphopeptide-amorphous calcium phosphate. Other embodiments of the oral care composition of the invention comprise a soluble calcium salt, e.g., selected from calcium sulfate, calcium chloride, calcium nitrate, calcium acetate, calcium lactate, and combinations thereof.

Potassium Source:

Yet further embodiments of the oral care composition of the invention comprise an orally acceptable potassium salt, e.g., potassium nitrate or potassium chloride, in an amount effective to reduce dentinal sensitivity. Some embodiments comprise from 0.1% to 7.5 wt % of an orally acceptable potassium salt, e.g., potassium nitrate and/or potassium chloride, based on the weight of the composition.

Some embodiments of the oral care composition of the invention are in the form of a toothpaste or alternatively a mouthrinse.

In some embodiments, the toothpaste optionally comprises one or more of water, an abrasive, a surfactant, a foaming agent, a vitamin, a polymer, an enzyme, a humectant, a thickener, an antimicrobial agent, a preservative, a flavoring, a colorant and/or a combination of two or more thereof.

Some embodiments of the oral care composition of the invention comprise a breath freshener, fragrance or flavoring. Other embodiments comprise an anti-calculus agent. In some embodiments, the anti-calculus agent is a polyphosphate, e.g., pyrophosphate, tripolyphosphate, or hexametaphosphate, e.g., in sodium salt form.

Some embodiments of the invention provide oral care compositions or methods to:

a. reduce or inhibit formation of dental caries,
b. reduce or inhibit demineralization and promote remineralization of the teeth, c. reduce or inhibit early enamel lesions,
d. reduce or inhibit gingivitis,
e. reduce levels of acid producing bacteria,
f. to increase relative levels of arginolytic bacteria,
g. inhibit microbial biofilm formation in the oral cavity,
h. raise and/or maintain plaque pH at levels of at least about pH 5.5 following sugar challenge,
i. reduce plaque accumulation,
j. whiten teeth,
k. improve whole body health,
l. reduce erosion of the teeth,
m. immunize or protect the teeth against cariogenic bacteria, and/or
n. clean the teeth and oral cavity.

The oral care compositions of the invention also may include an agent to increase the amount of foam that is produced when the oral cavity is brushed.

Illustrative examples of agents that increase the amount of foam include, but are not limited to polyoxyethylene and certain polymers including, but not limited to, alginate polymers.

The polyoxyethylene may increase the amount of foam and the thickness of the foam generated by the oral care carrier component of the oral care composition of the invention.

Polyoxyethylene is also commonly known as polyethylene glycol ("PEG") or polyethylene oxide. The polyoxyethylenes suitable for this invention will have a molecular weight of about 200,000 to about 7,000,000. In one embodiment the molecular weight will be about 600,000 to about 2,000,000 and in another embodiment about 800,000 to about 1,000,000. Polyox® is the trade name for the high molecular weight polyoxyethylene produced by Union Carbide.

The polyoxyethylene may be present in an amount of 1 to 90 wt %, in one embodiment 5 to 50 wt % and in another embodiment 10 to 20 wt % by weight of the oral care carrier component of the oral care compositions of the present invention. The dosage of foaming agent in the oral care composition (i.e., a single dose) is about 0.01 to 0.9 wt %, 0.05 to 0.5 wt %, and in another embodiment 0.1 to 0.2 wt %.

The oral care compositions of the invention may also include a flavoring agent.

Flavoring agents which are used in the practice of the present invention include, but are not limited to, essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange.

Also useful are such chemicals as menthol, carvone, and anethole. Certain embodiments employ the oils of peppermint and spearmint.

The flavoring agent may be incorporated in the oral composition at a concentration of 0.1 to 5 wt % and 0.5 to 1.5 wt %. The dosage of flavoring agent in the individual oral care composition dosage (i.e., a single dose) is 0.001 to 0.05 wt % and in another embodiment 0.005 to 0.015 wt %.

Sweetening agents which can be used include sucrose, glucose, saccharin, dextrose, levulose, lactose, mannitol, sorbitol, fructose, maltose, xylitol, saccharin salts, thaumatin, aspartame, D-tryptophan, dihydrochalcones, acesulfame and cyclamate salts, in particular sucralose, sodium cyclamate and sodium saccharin, and mixtures thereof. A composition preferably contains from 0.1 to 10 wt % of these agents, preferably from 0.1 to 1 wt %, based on the total composition.

The oral care compositions of the invention also may optionally include one or more chelating agents able to complex calcium found in the cell walls of the bacteria. Binding of this calcium weakens the bacterial cell wall and augments bacterial lysis.

Another group of agents suitable for use as chelating agents in the present invention are the soluble pyrophosphates. The pyrophosphate salts used in the present compositions can be any of the alkali metal pyrophosphate salts. In certain embodiments, salts include tetra alkali metal pyrophosphate, dialkali metal diacid pyrophosphate, trialkali metal monoacid pyrophosphate and mixtures thereof, wherein the alkali metals are sodium or potassium. The salts are useful in both their hydrated and unhydrated forms. An effective amount of pyrophosphate salt useful in the present composition is generally enough to provide at least about 1.0 wt % pyrophosphate ions, typically from 1.5 to 6 wt %, more typically from 3.5 to 6 wt % of such ions.

Gelled mineral oils are suitable hydrophobic viscosity modifiers. In some embodiments, the gelled mineral oil is preferably a blend of mineral oil and polyethylene, e.g. PLASTIGEL 5, which is a blend of 5% polyethylene in mineral oil, and is available from Pharmaceutical Resources/Lyne Laboratories Inc. of Brockton, Mass. Other suitable plastigels can be prepared in accordance with the teachings of Thau et al., "A New Procedure for the Preparation of Polyethylene-Mineral Oil Gels," J. Soc. Cosmetic Chemists, 16, 359-363 (1965). Suitable hydrophobic viscosity modifiers additional to gelled mineral oils, such as plastigels, can be identified by using the present disclosure as a guide.

The oral care compositions of the invention also optionally include one or more polymers. Polymers can provide certain advantages to the composition, for example when the composition is in the form of a toothpaste or gel, during preparation it is frequently necessary to add some thickening material to provide a desirable consistency of the composition, to provide desirable active release characteristics upon use, to provide shelf stability, and to provide stability of the composition, etc. Typical examples of polymers that can be present in the composition of the invention include polyethylene glycols, polyvinylmethyl ether maleic acid copolymers, polysaccharides (e.g., cellulose derivatives, for example carboxymethyl cellulose, or polysaccharide gums, for example gum karaya, gum arabic, gum tragacanth, xanthan gum or carrageenan gum). Acidic polymers, for example polyacrylate gels, may be provided in the form of their free acids or partially or fully neutralized water soluble alkali metal (e.g., potassium and sodium) or ammonium salts.

Particularly when noncationic antibacterial agents or antibacterial agents, e.g., triclosan, are included in any of the dentifrice components, there is also preferably included from 0.05 to 5 wt % of an agent which enhances the delivery and retention of the agents to, and retention thereof on oral surfaces. Such agents useful in the present invention are disclosed in U.S. Pat. Nos. 5,188,821 and 5,192,531; and include synthetic anionic polymeric polycarboxylates, such as 1:4 to 4:1 copolymers of maleic anhydride or acid with another polymerizable ethylenically unsaturated monomer, preferably methyl vinyl ether/maleic anhydride having a molecular weight (M.W.) of about 30,000 to about 1,000,000, most preferably about 30,000 to about 800,000. These copolymers are available for example as Gantrez. e.g., AN 139 (M.W. 500,000), AN 119 (M.W. 250,000) and preferably S-97 Pharmaceutical Grade (M.W. 700,000) available from ISP Technologies, Inc., Bound Brook, N.J. 08805. The enhancing agents when present are present in amounts ranging from 0.05 to 3 wt %.

A particular class of thickening or gelling agents includes a class of homopolymers of acrylic acid crosslinked with an alkyl ether of pentaerythritol or an alkyl ether of sucrose, or carbomers. Orally acceptable carbomers are commercially available from B. F. Goodrich.

In certain embodiments, thickening agents in an amount of 0.1 to 15.0 wt % by weight of the total composition are used, in another embodiment from 0.5 to 8 wt %, in another embodiment from 0.5 to 5 wt %.

In addition to the above described components, the embodiments of this invention can contain a variety of optional dentifrice ingredients some of which are described below. Optional ingredients include, for example, but are not limited to, adhesives, sudsing agents, additional antiplaque agents, and coloring agents.

The compositions of the invention can be made using methods which are common in the oral product area.

The actives of the present invention provide antiperspirant compositions that are stable at high pH, i.e., above 5, and as high as 10 or 11. Compositions containing the actives of the invention are thus effective at the higher pHs, and afford benefits over the traditional acidic antiperspirant compositions. These include avoiding the damage done to clothing by the traditional acidic compositions, affording benefits in reduced skin irritation.

solution before further base is added. The solution is allowed to react at 90° C. for 2 days under reflux. The amount of water added with calcium provides the final concentration.

Arginine was initially added to EACH solutions at varying concentrations, and heated gently at 50° C. overnight or at SOC for a shorter period of time. EACH is an aluminum sesquichlorohydrate (ASCH) antiperspirant (AP) active synthesized from $AlCl_3$, Glycine, and $CaCO_3$ or $Ca(OH)_2$, where the final composition is 3.75% Al, 6.54% Ca, and 8.80% Gly. To 6 g of EACH solution (3.75% Al), Arginine was added in a wide spectrum from 0.1 g to 6.96 g, yielding from 0.76% to 51.71% Arg w/w. The pH was found to increase logarithmically in a well fit manner. SEC showed that these Al species remained in peaks 3,4, and 5, and so no major transformation was obviously apparent, even across the pH barrier where formation of $Al(OH)_3$ is expected.

In addition, further basification with concentrated NaOH led to systems with a pH above ten, which were still stable. Significantly, basification of systems without Arginine led to the formation of gels or precipitates.

Further experiments were done to confirm these results and standardize the synthesis, and eventually samples with EACH were synthesized from 0.1% Arginine to 40% Arginine. This synthesis was at 50° C. for at least 3 days. The results can be seen in Table 1.

TABLE 1*

SEC Peak Distribution, Zeta Potential, and pH of EACH + Arginine Samples

| # | % Arg w/w theo. | g arg | % Arg w/w exp | % Peak 2 | % Peak 3 | % Peak 4 | % Peak 5 | pH** | Zeta Pot. |
|---|---|---|---|---|---|---|---|---|---|
| 1 | 0.10% | 0.0114 | 0.09% | 0 | 1.14 | 92.36 | 6.5 | 2.84 | 18.5 |
| 2 | 0.50% | 0.0623 | 0.47% | 0 | 0.8 | 94.71 | 4.48 | 2.88 | 12.5 |
| 3 | 1.00% | 0.1336 | 1.01% | 0.59 | 1.28 | 95.41 | 2.72 | 3.12 | 18.3 |
| 4 | 2.50% | 0.3367 | 2.51% | 1.03 | 6.5 | 90.06 | 2.41 | 4.66 | 4.74 |
| 5 | 5.00% | 0.6960 | 5.03% | 1.29 | 26.53 | 69.25 | 2.93 | 5.56 | 5.23 |
| 6 | 10.00% | 1.4765 | 10.15% | 0.84 | 21.82 | 73.51 | 3.83 | 6.5 | 9.92 |
| 7 | 15.00% | 2.2881 | 15.01% | 0.3 | 21.78 | 70.67 | 7.25 | 7.07 | 24 |
| 8 | 20.00% | 3.2062 | 19.74% | 0.55 | 33.47 | 58.18 | 7.8 | 7.49 | 7.78 |
| 9 | 25.00% | 4.2550 | 24.61% | 0.82 | 35.85 | 54.96 | 8.36 | 7.76 | 5.19 |
| 10 | 30.00% | 5.7129 | 30.39% | 0.44 | 37.16 | 55.16 | 6.79 | 8.13 | 15.3 |
| 11 | 35.00% | 6.9793 | 34.90% | 0.74 | 34.47 | 51.93 | 12.86 | 8.5 | 11.4 |
| 12 | 40.00% | 8.6104 | 39.78% | 1.49 | 39.73 | 54.13 | 4.65 | 8.49 | 12.7 |

Each of the patents, applications and printed publications mentioned herein are incorporated by reference in their entireties for all purposes, as are each of the following US and International patent applications: PCT/US2012/033926, US 2015-0132242; PCT/US2013/032391, U.S. Ser. No. 14/770,142, filed Aug. 25, 2015; PCT/US2007/087145, US 2010-0202993.

EXAMPLES

Example 1: EACH/Arginine Actives

EACH was prepared according to the procedure of PCT/US2013/032391, filed Mar. 15, 2013, incorporated by reference herein in its entirety. The starting materials consists of $AlCl_3$ $6H_2O$, $Ca(OH)_2$ or $CaCO_3$, and Glycine. The amounts used differ and can be inferred from the final composition, but generally have final concentrations of 1.0 M [$Al^{3+}$], 1.2 M [$Ca^{2+}$], and 1.2M [Gly]. The reaction is as follows: $AlCl_3$ and Gly are made into a concentrated solution (1.2M Al, 1.44M Gly) and heated to 90° C. under reflux. Calcium hydroxide is added in small portions so that each portion has enough time to dissolve/react and create a clear Samples 1-12 in Table 1 were synthesized as follows. A set amount of arginine was added directly into EACH solution and the samples were vortexed until all or most of the solid appeared to be in contact with the solution. The samples were then heated for 3 days at 50° C. in an oven and yielded clear solutions. Table 2 below shows the composition of the samples.

TABLE 2

Composition of Arginine-EACH Samples

| Sample | % w/w sample | g Arg | g EACH | % Arg | % Al | % $H_2O$ |
|---|---|---|---|---|---|---|
| 1 | 0.10% | 0.0114 | 13.2 | 0.09% | 3.75% | 60.56% |
| 2 | 0.50% | 0.0623 | 13.191 | 0.47% | 3.73% | 60.33% |
| 3 | 1% | 0.1336 | 13.059 | 1.01% | 3.71% | 60.00% |
| 4 | 2.50% | 0.3367 | 13.063 | 2.51% | 3.66% | 59.09% |
| 5 | 5% | 0.6960 | 13.131 | 5.03% | 3.56% | 57.56% |
| 6 | 10% | 1.4765 | 13.065 | 10.15% | 3.37% | 54.46% |
| 7 | 15% | 2.2881 | 12.9573 | 15.01% | 3.19% | 51.51% |
| 8 | 20% | 3.2062 | 13.035 | 19.74% | 3.01% | 48.64% |
| 9 | 25% | 4.2550 | 13.038 | 24.61% | 2.83% | 45.70% |
| 10 | 30% | 5.7129 | 13.088 | 30.39% | 2.61% | 42.19% |

TABLE 2-continued

Composition of Arginine-EACH Samples

| Sample | % w/w sample | g Arg | g EACH | % Arg | % Al | % H$_2$O |
|---|---|---|---|---|---|---|
| 11 | 35% | 6.9793 | 13.0199 | 34.90% | 2.44% | 39.46% |
| 12 | 40% | 8.6104 | 13.035 | 39.78% | 2.26% | 36.50% |

The results show the consistency in the increase in pH, as well as peak 3 and 4 stability at high pH. To confirm that cationic aluminum clusters were still present in solution, zeta-potential measurements were taken, and all solutions, regardless of concentration, yielded clearly positive zeta-potentials, indicating that there was still a positive surface charge present on the largest clusters. Other characterization of the molecule was carried out to ensure that the clusters were still present, including $^{27}$Al NMR and size-exclusion chromatography.

Upon dilution to 0.1% Al solutions (w/w) the solutions with a pH higher than 7 formed precipitate. Note that dilutions ranged from 37.5× to 22.5×. This indicates that the species are not exempt from high pH effects, but are stable in that form at high concentrations. After several months, these concentrated solutions retained clarity, and so the precipitate formation is only after direct dilution.

Example 2: ACH/Arginine Actives

To obtain a system similar to that seen with the EACH/Arginine system in Example 1, ACH (25.6% Al, 16.7% Cl w/w) with CaCl$_2$ and L-Arginine were tested. It was initially found that adding arginine directly to concentrated ACH (aluminum chlorohydrate) solutions resulted in the formation of gels, and did not aid in forming a stable solution. Work was done to develop a system which stabilized the arginine and increased solubility to levels seen in the EACH system.

A number of different systems were able to be developed, and as an example, ACH, Arginine, and CaCl$_2$ solution was synthesized at 3% Al, 5% Ca, and 49% arginine.

Zeta-potential measurements for these ACH samples also were found to be positive, and SEC confirmed the presence of peaks 3 and 4. Exemplary formulations are seen in Table 3 below:

TABLE 3

SEC, ZP and pH of ACH + Ca + Arginine Samples

| Sample | % Arg | % Al | % Ca | % ACH | Peak 3 | Peak 4 | Peak 5 | pH | ZP |
|---|---|---|---|---|---|---|---|---|---|
| LC4 | 38.47 | 2.63 | 4.57 | 10.34 | 39.23 | 50.62 | 10.14 | 9.04 | 29.9 |
| HC4 | 42.72 | 3.03 | 5.26 | 11.91 | 31.92 | 54.66 | 13.42 | 8.71 | 9.37 |

Samples LC4 and HC4 were prepared as follows. A solid mixture of ACH and CaCl$_2$ was prepared (1 g ACH per 1.62 g of CaCl$_2$ 2H$_2$O). Two solutions were prepared, a high concentration and low concentration. The low concentration was 38.5% w/w of the ACH/CaCl$_2$ mixture (3.73% Al) and the high was 55.8% mixture (5.41% Al). Note that these solutions were not clear. Arginine was added to both solutions and allowed to sit at 50 C for 3 days. Note that Arginine should be added to a solution, and not solution added to Arginine. Adding a solution to Arginine can create a barrier between Arginine and the solution which takes longer to react, or in some cases will not react after prolonged or high temperature heating.

Polymerization and size distribution of antiperspirant actives in aqueous solution was monitored by size exclusion chromatography, or SEC-HPLC. The relative retention time for each peak varies with experimental conditions, but the peaks remain relative to each other for set conditions. SEC data as collected with a Water®600 analytical pump and controller, Rheodyne®7725I injector utilizing a Protein-Pak® 125 (Waters) column and Waters 2414 Refractive Index Detector.

Example 3: Aluminum Chloride Active

Aluminum chloride in the hexahydrate form was combined with calcium chloride in water so that the solution was 3.60% Al, 6.42% Ca, and 44.3% added H$_2$O. Arginine was added directly to the solution so that the final weight percent of Arginine was from 0.01 to 60 wt. %, or preferably from 0.01 to 50 wt. %, or preferably from 10-40 wt. %. In one instance the molar ratio of Arginine added to Al was 2.5 (37% Arg).

Example 4—Water Treatment

A) EACH/Arginine

Water treatment with synthetic waste water and a protein precipitant test with BSA were conducted with the EACH samples, to ensure that the samples were capable of interacting with basic surfactants and proteins.

For water treatment an artificial waste water [constructed with several commercial surfactants], the ACH with Ca/Arg, EACH with Arg, EACH, and ACH samples were tested against an untreated sample. The Al concentration in all samples was adjusted to 1% Al (w/w) and 1 mL of the samples was added to 50 mL of waste water and shaken vigorously for 30 seconds. The Samples had the following compositions shown in Table 4:

TABLE 4

Waste Water Sample Compositions

| Sample | Composition |
|---|---|
| A | 40% Arg-EACH |
| B | 30% Arg-EACH |
| C | 10% Arg-EACH |
| D | 1% Arg-EACH |
| E | EACH |
| F | ACH |
| G | Untreated |

The EACH and Arginine samples all exhibited high turbidity removal, and the samples were clear after less than 15 minutes. The main difference for the samples was in removing surface layer surfactants (above liquid interface), and forming floc. Samples B and C removed more surface layer bubbles than EACH or other samples, and formed significant amounts of flocs. Over the weekend 30% Arg-EACH had the highest amounts of floc, more than EACH. The BSA experiment showed that while all samples precipitated or formed a gel, the BSA-Al sample formed a floc.

B) ACH/Arginine

Water treatment with synthetic waste water and a protein precipitant test with BSA were also conducted with the ACH and EACH samples, to ensure that the samples were capable of interacting with basic surfactants and proteins. In general, similar to EACH samples, HC4 and LC4 precipitate upon dilution.

The test procedure was the same as for the EACH/Arginine samples, which are summarized below in Table 5:

TABLE 5

Waste Water Sample Compositions

| Sample | Composition |
|---|---|
| H | HC4 (ACH + Ca/Arg) |
| I | LC4 (ACH + Ca/Arg) |
| J | 40% Arg-EACH |
| K | 30% Arg-EACH |
| L | 10% Arg-EACH |
| M | 1% Arg-EACH |
| N | EACH |
| O | ACH |
| P | Untreated |

The ACH/EACH+Arginine samples (H—N) all exhibited high turbidity removal, and the samples were clear after less than 15 minutes. The main difference for the samples was in removing surface layers surfactants (above liquid interface), and forming floc. Samples (H), (K), and (L) removed more surface layer bubbles than EACH or other samples, and formed significant amounts of flocs. Over the weekend it was seen that HC4 and 30% Ara EACH had the highest amounts of floc, more than EACH.

Similar to above, the BSA experiment showed that while all samples precipitated or formed a gel, the BSA-Al sample formed a floc.

These data show that the high pH antiperspirants of the invention effectively aggregate with anionic species present in waste water.

Example 5—Oral Care

The actives of the invention are incorporated into oral care compositions in according to the teachings of PCT/US2013/032391 (U.S. Ser. No. 14/770,142, filed Aug. 25, 2015), which are incorporated herein by reference for all purposes.

What is claimed is:

1. An active comprising:
   i) an aluminum system active, comprising one or both of:
      an aluminum active comprising chloride ions, and having a metal to chloride ratio of from 0.3 to 3; and/or
      an aluminum active comprising or derived from aluminum zirconium glycine salts;
   ii) a buffer comprising arginine; and
   iii) a calcium ion source, wherein the calcium ion is 6-8% by weight based on the total composition;
   wherein the composition has a pH greater than 6;
   wherein the aluminum active is stable at the pH; and
   wherein the aluminum active comprises an aluminum chloride compound having an aluminum to chloride molar ratio of 0.3:1 to 3:1 exhibiting a Size Exclusion Chromatography (SEC) chromatogram having a SEC Peak 4 to Peak 3 intensity ratio of at least 7 and a Peak 4 intensity greater than a Peak 5 intensity in aqueous solution.

2. The active of claim 1, wherein the aluminum active comprises or is derived from aluminum monochlorohydrate, aluminum dichlorohydrate, or aluminum sesquichlorohydrate.

3. The active of claim 1, wherein the aluminum active comprises or is derived from aluminum sesquichlorohydrate.

4. The active of claim 3, wherein the aluminum active is derived from $AlCl_3$, glycine, and $CaCO_3$ or $Ca(OH)_2$, where the final composition is about 3-4% Al, and about 8-9% glycine.

5. The active of claim 4, comprising from about 12% to about 14% of said aluminum active; and from about 0.1% to about 50% arginine as the buffer.

6. The active of claim 1, further comprising zirconium in a molar ratio of aluminum to zirconium of about 5:1 to about 10:1.

7. The active of claim 1, wherein the ratio of the wt % of arginine to the wt % of the aluminum containing active is from 8:1 or from 1:2 to 2:1; or from 3:1 to 5:1.

8. The active of claim 7, wherein the aluminum chlorohydrate (ACH) active has a composition comprising 3-5% Al, 14-17% Cl, 13-17% Arginine, and 15-17% of an active ACH having 25-26% Al, 16-17% Cl, and wherein 48-49% of the composition is present as $Al_2O_3$.

9. The active of claim 1, wherein the active is prepared by a method comprising the steps of:
   preparing a solution comprising the aluminum active and the calcium ion source; and
   adding the buffer to the solution to form a second solution; and
   optionally further comprising the step of adjusting the pH of the second solution to a pH greater than 6.

10. The active of claim 1, wherein the buffer comprises arginine and/or a salt form thereof; and the calcium ion source comprises $CaCl_2$ or $Ca(OH)_2$.

11. The active of claim 1, wherein the active comprises an aluminum zirconium glycine salt.

12. An antiperspirant comprising the active of claim 1.

13. A method for the preparation of an aluminum containing active having a pH greater than 6; wherein the aluminum active is stable at the pH; comprising the steps of:
   preparing a solution comprising an aluminum active and a calcium ion source; and
   adding a buffer to the solution to form a second solution; wherein:
   the aluminum active either (i) comprises chloride ions, and has a metal to chloride ratio of from 0.3 to 3; and/or (ii) comprises or is derived from aluminum zirconium glycine salts; and
   the buffer comprises urea or an amino acid in free or salt form.

14. A method of preventing or controlling perspiration comprising contacting the skin of a person with an antiperspirant composition according to claim 12.

15. A method of treating polluted water comprising contacting the water with an active according to claim 1.

* * * * *